United States Patent
Iwasaki (10) Patent No.: US 9,837,223 B2
(45) Date of Patent: Dec. 5, 2017

(54) TOUCH PANEL (71) Applicant: FUJITSU COMPONENT LIMITED, Tokyo (JP)

(72) Inventor: Nobuya Iwasaki, Tokyo (JP)

(73) Assignee: FUJITSU COMPONENT LIMITED, Tokyo (JP)

( * ) Notice: Subject to any disclaimer, the term of this patent is extended or adjusted under 35 U.S.C. 154(b) by 386 days.

(21) Appl. No.: 13/939,333

(22) Filed: Jul. 11, 2013

(65) Prior Publication Data
US 2014/0042000 A1 Feb. 13, 2014

(30) Foreign Application Priority Data

Aug. 9, 2012 (JP) ................. 2012-177297

(51) Int. Cl.
*H01H 9/02* (2006.01)
*H01H 11/00* (2006.01)
*G06F 3/041* (2006.01)

(52) U.S. Cl.
CPC ............. *H01H 9/02* (2013.01); *G06F 3/041* (2013.01); *H01H 11/00* (2013.01); *B32B 2457/202* (2013.01); *G06F 2203/04103* (2013.01); *Y10T 156/1062* (2015.01)

(58) Field of Classification Search
None
See application file for complete search history.

(56) References Cited

U.S. PATENT DOCUMENTS

| | | | |
|---|---|---|---|
| 2009/0242283 A1* | 10/2009 | Chiu | G06F 3/044 178/20.01 |
| 2010/0013786 A1* | 1/2010 | Nishikawa | G06F 1/1624 345/173 |
| 2011/0102346 A1* | 5/2011 | Orsley | G06F 3/044 345/173 |
| 2011/0199330 A1* | 8/2011 | Hsu | G06F 3/044 345/174 |
| 2011/0242057 A1* | 10/2011 | Lee | G06F 3/041 345/176 |
| 2011/0298739 A1* | 12/2011 | Wu | G06F 3/041 345/173 |

FOREIGN PATENT DOCUMENTS

JP 2011-113461 6/2011

OTHER PUBLICATIONS

Patent Abstracts of Japan, Publication No. 2011-113461, Published Jun. 9, 2011.

* cited by examiner

*Primary Examiner* — Anthony J Frost
(74) *Attorney, Agent, or Firm* — Staas & Halsey LLP (57) ABSTRACT

A touch panel includes: a body connected to wiring drawn out to the outside of the touch panel; a sheet member to which decoration printing is added; an adhesive that pastes the sheet member on the body and is the same size as the sheet member; and a non-adhesion film formed between the adhesive and the wiring.

8 Claims, 7 Drawing Sheets

(step S11) DECORATION PRINTING (step S12) PASTE OCA (step S13) FORM NON-ADHESION FILM (step S14) CUT DECORATION FILM
(step S15) PASTE DECORATION FILM

FIG. 6

TOUCH PANEL

CROSS-REFERENCE TO RELATED APPLICATION

This application is based upon and claims the benefit of priority of the prior Japanese Patent Application No. 2012-177297 filed on Aug. 9, 2012, the entire contents of which are incorporated herein by reference.

FIELD

A certain aspect of the embodiments is related to a touch panel and a method for manufacturing the same.

BACKGROUND

There has been known a touch panel in which a protective sheet has been pasted on an operation surface thereof (e.g. see Japanese Laid-open Patent Publication No. 2011-113461). To transmit vibration of the touch panel to a user effectively, in the touch panel, a non-adhesion part which is not pasted on the peripheral part of the touch panel is formed on the peripheral part of the protective sheet.

Figure 1:
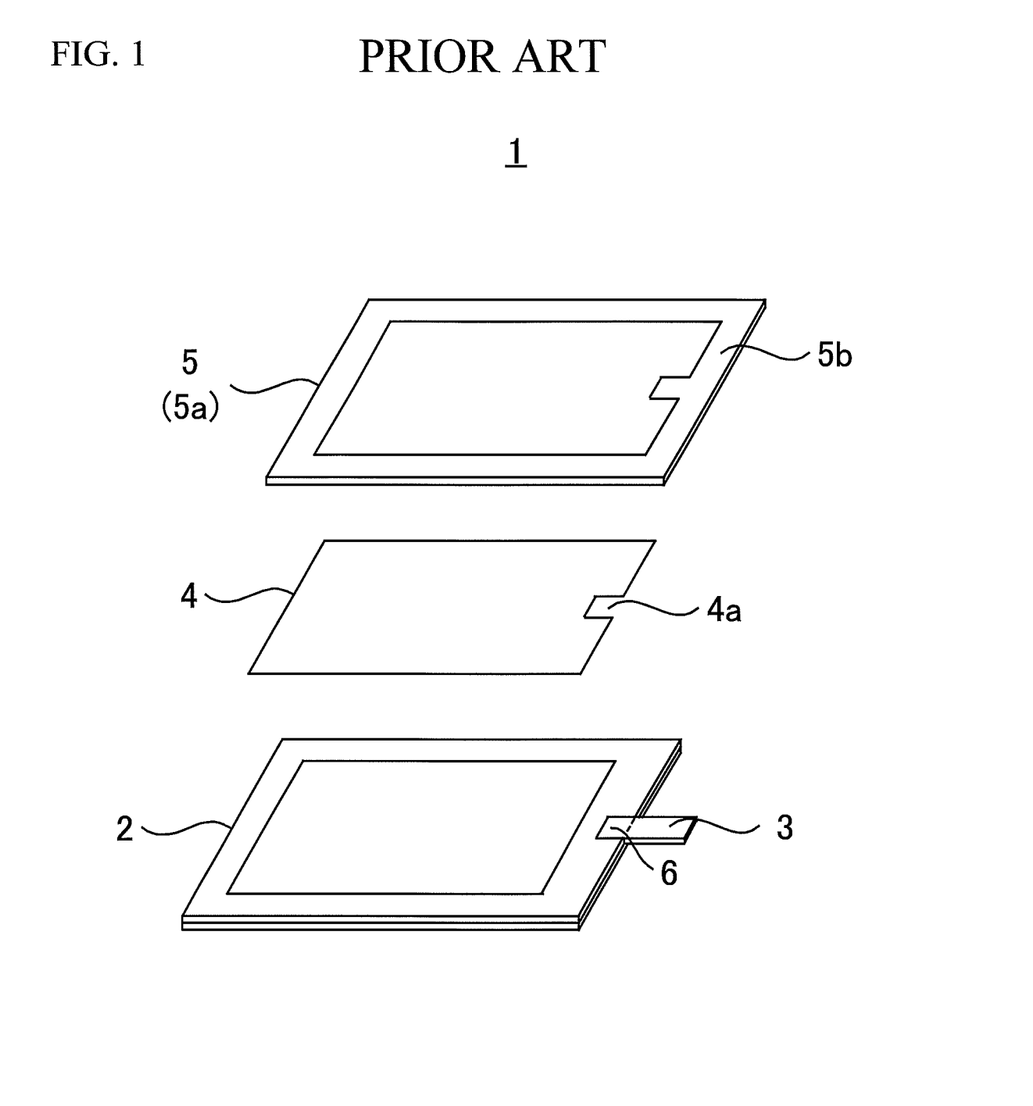
FIG. 1 is an exploded diagram of a conventional touch panel.
Figure 2A:
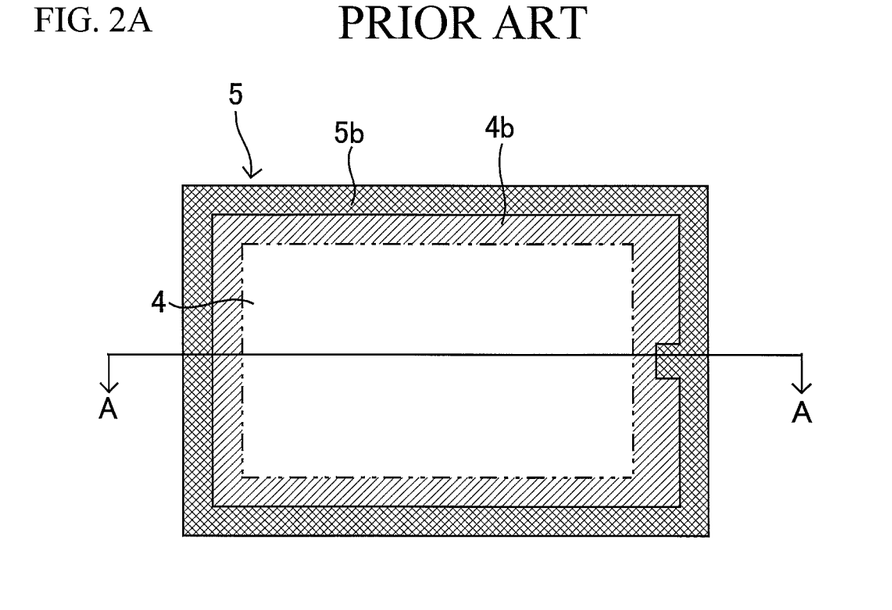
FIG. 2A is a schematic diagram of the conventional touch panel, as viewed from above.
Figure 2B:
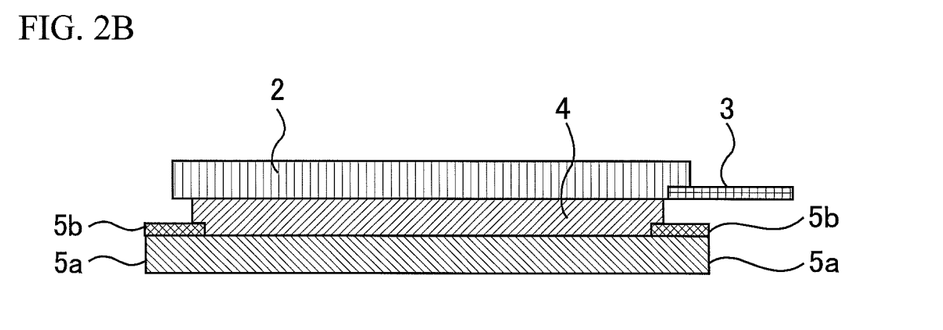
FIG. 2B is a cross-section diagram taken on a line A-A of FIG. 2A.

FIG. 1 is an exploded diagram of a conventional touch panel. FIG. 2A is a schematic diagram of the conventional touch panel, as viewed from above. FIG. 2B is a cross-section diagram taken on a line A-A of FIG. 2A. FIG. 2B illustrates a state where the touch panel of FIG. 2A is reversed (i.e., an operation surface is placed at a lowest position).

In FIG. 1, the touch panel 1 includes a touch panel body 2, an FPC (Flexible Printed Circuit) 3 including a wiring for a transparent electrode, an OCA (Optical Clear Adhesive) 4 for pasting a decoration film 5 on the touch panel body 2. The decoration film 5 is for improving a design characteristic of the appearance of the touch panel 1. The decoration film 5 is made of a PET (Polyethylene terephthalate) film 5a, and decoration printing 5b for appearance design is added to a periphery of the PET film 5a.

The OCA 4 has a cut-out portion 4a at a position opposite to the FPC 3, and is not arranged on the FPC 3. This is because, when the OCA 4 has no cut-out portion 4a, in a connection portion 6 (namely, a wiring portion of the FPC 3 connected to the touch panel body 2), the OCA 4 follows unevenness of the connection portion 6 and a flat characteristic of the operation panel (i.e., the decoration film 5) is lost. Moreover, a reason why the OCA 4 is not arranged on the FPC 3 is that the connection portion 6 of the FPC 3 and the decoration film 5 are fixed to the OCA 4 and hence the connection portion 6 can be damaged by the heat contraction of the OCA 4 and the decoration film 5.

Figure 3:
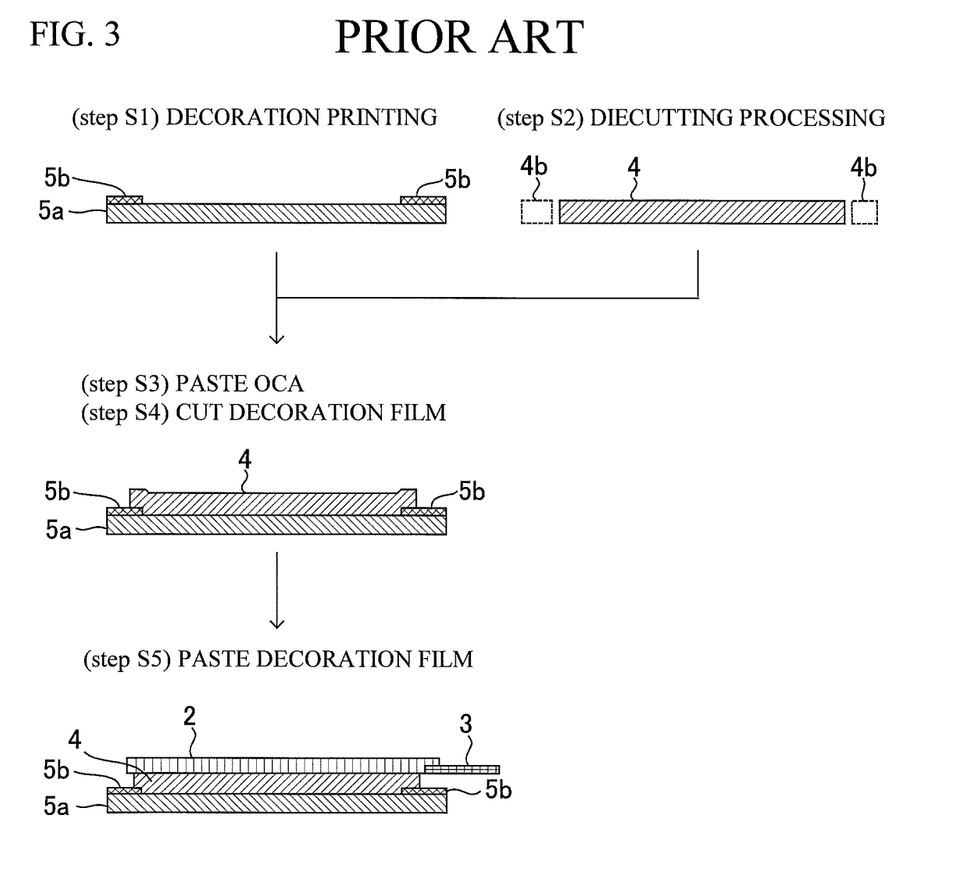
FIG. 3 is a diagram illustrating a method for manufacturing the conventional touch panel.

FIG. 3 illustrates a method for manufacturing the touch panel 1 indicated by FIGS. 1A, 2A and 2B. As a device for manufacturing the touch panel, a well-known device is used.

First, the decoration printing 5b is added to a periphery of the PET film 5a (step S1). Then, the OCA 4 is processed into a shape as illustrated in FIG. 1 by die cutting processing (step S2). Here, as illustrated in FIGS. 2A and 3, a portion 4b of the OCA 4 corresponding to the connection portion 6 of the FPC 3 and a periphery is removed by the die cutting processing.

Next, the processed OCA 4 is pasted on the PET film 5a to which the decoration printing 5b is added (step S3). Then, the PET film 5a on which the OCA 4 is pasted is cut in a suitable shape (step S4). The cut PET film 5a is pasted on the touch panel body 2 (step S5). It should be noted that a plurality of PET films for touch panel are obtained from the PET film 5a on which the OCA 4 of step S4 is pasted.

SUMMARY

According to an aspect of the present invention, there is provided a touch panel including: a body connected to wiring drawn out to the outside of the touch panel; a sheet member to which decoration printing is added; an adhesive that pastes the sheet member on the body and is the same size as the sheet member; and a non-adhesion film formed between the adhesive and the wiring.

The objects and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

In the conventional touch panel, since the diecutting processing is necessary for the OCA 4 as described above, the expense for manufacturing a metallic mold for diecutting is required, and hence the manufacturing cost increases. On the other hand, when the diecutting processing is not performed, there is a possibility that the connection portion 6 of the FPC 3 (i.e., the wiring portion of the FPC 3) is damaged as described above.

Hereinafter, a description will be given of embodiments of the present invention with reference to the drawings.

First Embodiment

Figure 4A:
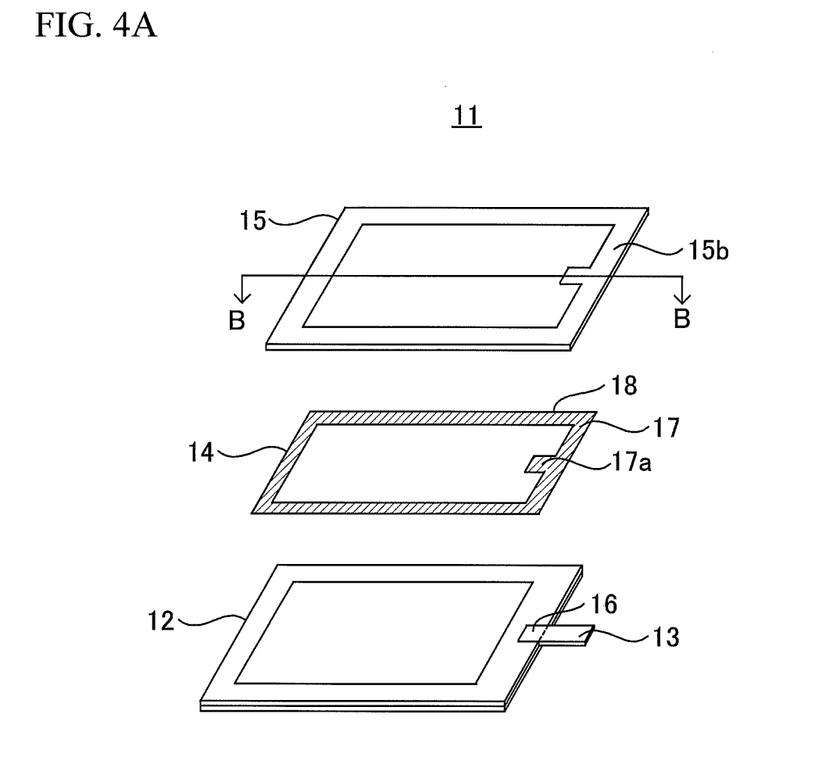
FIG. 4A is an exploded diagram of a touch panel according to a first embodiment.
Figure 4B:
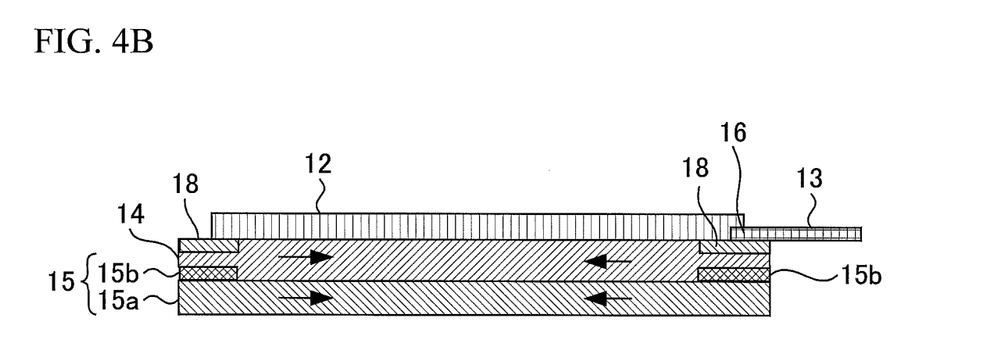
FIG. 4B is a cross-section diagram taken on a line B-B of FIG. 4A.

FIG. 4A is an exploded diagram of a touch panel according to a first embodiment. FIG. 4B is a cross-section diagram taken on a line B-B of FIG. 4A. FIG. 4B illustrates a state where the touch panel of FIG. 4A is reversed (i.e., an operation panel is placed at a lowest position).

In FIG. 4A, a touch panel 11 includes: a well-known resistive film-type or projected capacitive-type touch panel body 12; an FPC (Flexible Printed Circuit) 13 including a wiring for a transparent electrode; an OCA (Optical Clear Adhesive) 14 for pasting a decoration film 15 on the touch panel body 12; and the decoration film 15 for improving a design characteristic of the appearance.

The decoration film 15 is an operation surface for inputting operation against the touch panel body 12, and is made of a PET (Polyethylene terephthalate) film 15*a*. Decoration printing 15*b* for appearance design is added to a periphery of the PET film 15*a*. The decoration film 15 may be made of Polycarbonate or glass, instead of the PET film.

A non-adhesion film 18 is formed on a periphery 17 of the OCA 14 including an area 17*a* on the OCA 14 which is opposed to a connection portion 16. Thereby, the stress caused by the heat contraction of adhesives or a sheet member is equally applied to the operation surface of the touch panel body 12.

The non-adhesion film 18 is formed by printing an ink containing non-adhesives, such as silicon, on the periphery 17 of the OCA 14, or spraying an ink on the periphery 17 of the OCA 14. The thickness of the non-adhesion film 18, i.e., the thickness of the ink containing non-adhesives is 3 to 5 µm. This is because a minimum thickness is 3 to 5 µm when the ink containing non-adhesives is printed or sprayed using a well-known device. Here, the non-adhesion film 18 may be formed by a film containing non-adhesives, such as silicon. Then, the non-adhesion film 18 is formed on the OCA 14 near the touch panel body 12, as illustrated in FIG. 4B.

The FPC 13 is connected to an end of the touch panel body 12. The connection portion 16 of the FPC 13, i.e., a wiring portion of the FPC 13 connected to the touch panel body 12, contacts the non-adhesion film 18, as illustrated in FIG. 4B. Thereby, even if the stress toward a central direction (e.g. arrows of FIG. 4B) acts on the OCA 14 by the contraction of the decoration film 15, for example, the stress does not act on the connection portion 16 of the FPC 13. Therefore, the connection portion 16 of the FPC 13 won't be damaged by the contraction of the decoration film 15.

Figure 5:
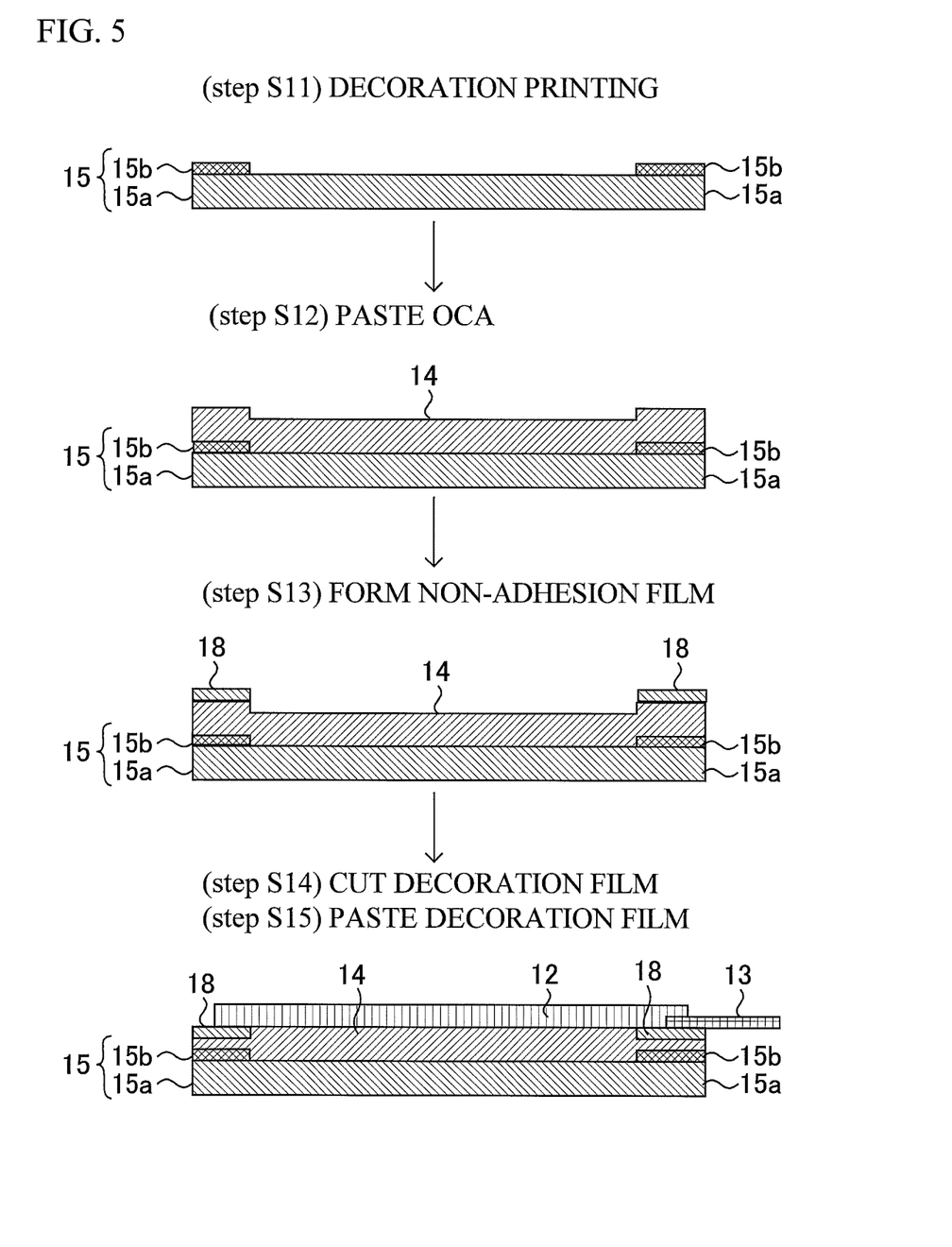
FIG. 5 is a diagram illustrating a method for manufacturing the touch panel according to the first embodiment.

FIG. 5 is a diagram illustrating a method for manufacturing the touch panel 11. As a device for manufacturing the touch panel 11, a well-known device is used.

First, the decoration printing 15*b* is added to a periphery of the PET film 15*a* (step S11). Next, the OCA 14 is pasted on the PET film 15*a* to which the decoration printing 15*b* was added (step S12). Next, the ink containing the non-adhesives is printed on the periphery 17 of the OCA 14 or sprayed on the periphery 17 of the OCA 14 (step S13). Thereby, the non-adhesion film 18 is formed on the circumference part 17 of the OCA 14.

Then, the PET film 15*a* on which the OCA 14 is pasted is cut in a desired shape (step S14). Therefore, the OCA 14 is the same size as the PET film 15*a* in planar view. It should be noted that a plurality of PET films for touch panel are obtained from the PET film 15*a* on which the OCA 14 is pasted. The desired shape described above is slightly larger than the touch panel body 12. Finally, the cut PET film 15*a* is pasted on the touch panel body 12 (step S15).

Thus, according to the method for manufacturing the touch panel 11, the diecutting processing of the OCA 14 is unnecessary, and hence the expense for manufacturing the metallic mold for diecutting is not required. Therefore, the manufacturing cost can be reduced, as compared with the method for manufacturing the conventional touch panel. If the diecutting processing of the OCA 14 is performed, it is necessary to paste the OCA 14 on the decoration film 15 with high precision. However, since in the method for manufacturing the touch panel 11 of FIG. 5, the diecutting processing of the OCA 14 is not performed, highly precise pasting is not required, and hence there is a merit that manufacture of the touch panel becomes easy.

As described above, according to the present embodiment, the touch panel 11 includes: the touch panel body 12 connected to the wiring drawn out to the outside of the touch panel, i.e., the FPC 13; the decoration film 15 to which the decoration printing is added; the OCA 14 that pastes the decoration film 15 on the touch panel body 12 and is the same size as the decoration film 15; and the non-adhesion film 18 formed between the OCA 14 and the FPC 13.

Therefore, the wiring of the FPC 13 does not receive the stress according to the heat contraction of the adhesives or the sheet member, so that the damage of the wiring can be avoided. Since the OCA 14 is the same size as the decoration film 15, the metallic mold for diecutting is not required, and hence the manufacturing cost can be reduced.

Moreover, since in touch panel 11, a space is not formed between the decoration film 15 and the touch panel body 12, the problem that a foreign matter adheres to the OCA 14 and the yield of manufacture gets worse is solved. In addition since the non-adhesion film 18 is a thin film formed by printing or spraying, the operation surface, i.e., the flat characteristic of the decoration film 15 is not affected.

Second Embodiment

The present embodiment is different from the first embodiment in a position where the non-adhesion film 18 is formed. Hereinafter, a description will be mainly given of features different from the first embodiment.

Figure 6:
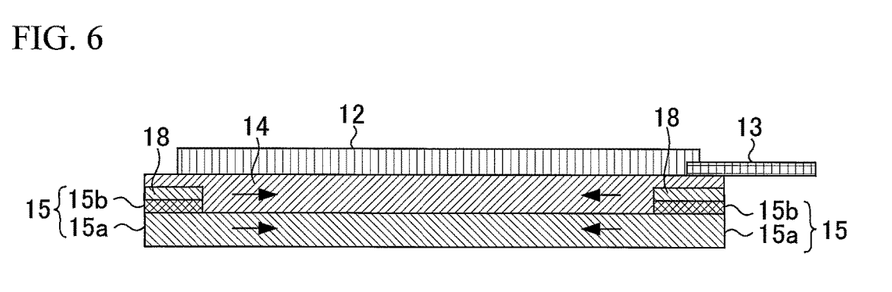
FIG. 6 is a cross-section diagram of the touch panel according to a second embodiment.

FIG. 6 is a cross-section diagram illustrating a variation of the touch panel 11.

The non-adhesion film 18 is formed by printing an ink containing non-adhesives, such as silicon, on the decoration printing 15*b*, or spraying an ink on the decoration printing 15*b*. Moreover, the OCA 14 is pasted on the non-adhesion film 18, and the connection portion 16 of the FPC 13 is pasted on the OCA 14. In this case, even if the stress toward a central direction (e.g. arrows of FIG. 6) acts on the OCA 14 by the heat contraction of the decoration film 15, for example, the non-adhesion film 18 functions so as to reduce the stress, and hence the stress rarely acts on the connection portion 16 of the FPC 13. Therefore, it is possible to restrain the connection portion 16 of the FPC 13 from being damaged by the heat contraction of the decoration film 15.

Figure 7:
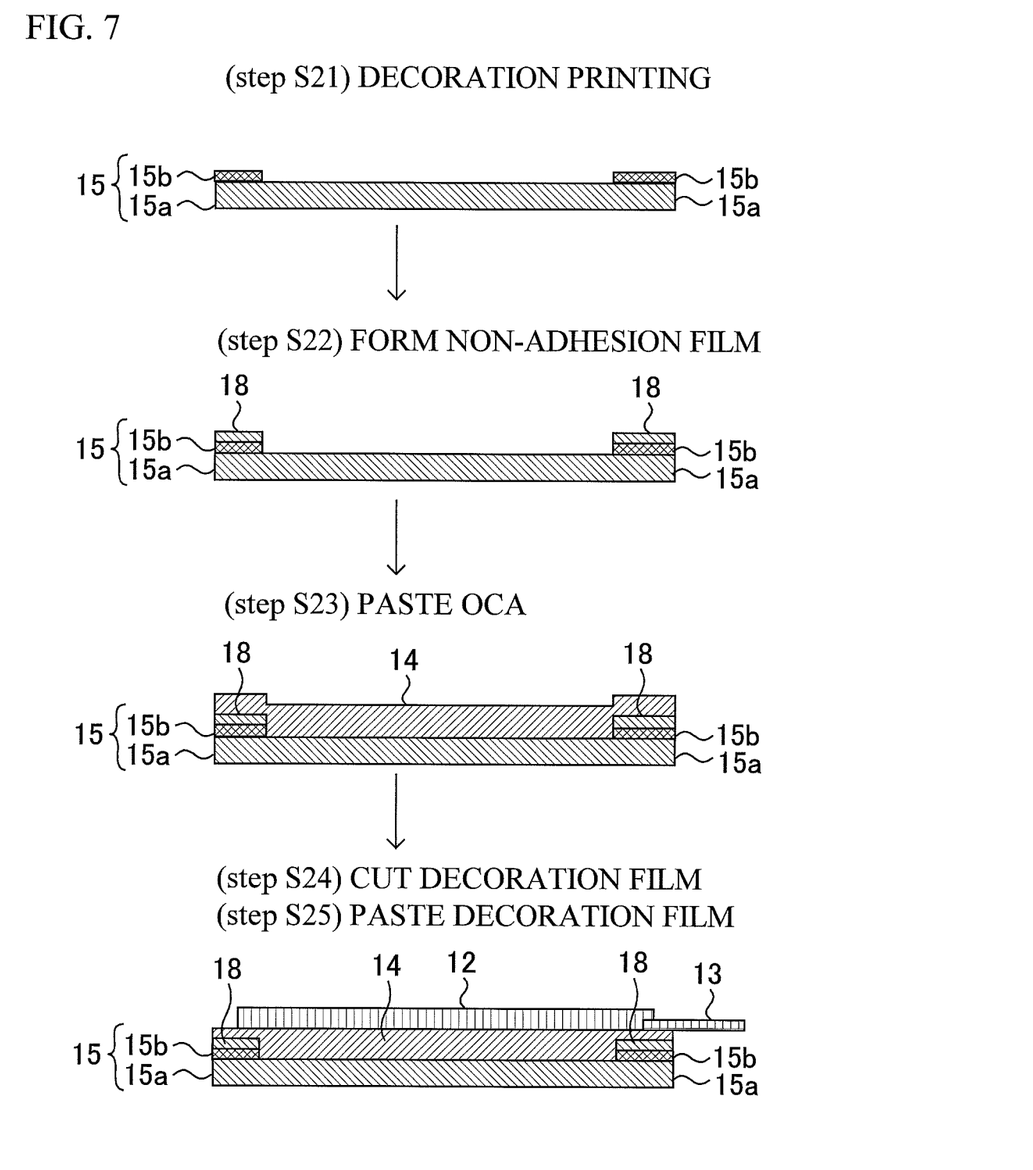
FIG. 7 is a diagram illustrating a method for manufacturing the touch panel according to the second embodiment.

FIG. 7 is a diagram illustrating the method for manufacturing the touch panel 11. As a device for manufacturing the touch panel 11, a well-known device is used.

First, the decoration printing 15*b* is added to a periphery of the PET film 15*a* (step S21). Next, the ink containing the non-adhesives is printed on the decoration printing 15*b* or sprayed on the decoration printing 15*b* (step S22). Thereby, the non-adhesion film 18 is formed on the decoration printing 15*b*.

Next, the OCA 14 is pasted on the PET film 15*a* on which the decoration printing 15*b* and the non-adhesion film 18 are stacked (step S23). Then, the PET film 15*a* on which the OCA 14 is pasted is cut in a desired shape (step S24). Therefore, the OCA 14 is the same size as the PET film 15*a* in planar view. It should be noted that a plurality of PET films for touch panel are obtained from the PET film 15*a* on which the OCA 14 is pasted. The desired shape described above is slightly larger than the touch panel body 12. Finally, the cut PET film 15*a* is pasted on the touch panel body 12 (step S25).

As described above, according to the present embodiment, the non-adhesion film 18 is formed between the OCA 14 and the decoration printing 15*b*. The wiring of the FPC 13 rarely receives the stress according to the heat contraction of the adhesives or the sheet member, so that damage to the wiring can be avoided.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A touch panel, comprising:
a body having a first surface and containing a recess formed in a peripheral edge of the first surface;
a metal wiring connected to and extending from the body;
a first layer having a first surface;
decoration formed on a periphery of the first surface of the first layer;
a second layer which is adhesive and has a first surface that adheres to the first surface of the body, and a second surface that adheres to the first surface of the first layer, and a recess formed in a peripheral edge of the first surface of the second layer;
wherein the second layer has the same outer dimensions as the first layer; and
a third layer which is non-adhesive and is formed between a portion of a periphery of the first surface of the second layer and the first surface of the body, and contacts the metal wiring without adhering to the metal wiring.

2. The touch panel according to claim 1, wherein the third layer is ink containing at least one non-adhesive.

3. The touch panel according to claim 1, wherein the third layer is formed on an area of the periphery of the first surface of the second layer which is opposed to the wiring.

4. The touch panel according to claim 1, wherein the thickness of the third layer is 3 to 5 µm.

5. The touch panel according to claim 1, wherein the decoration is made of one of polyethylene terephthalate, polycarbonate or glass.

6. A touch panel, comprising:
a body having a first surface and containing a recess formed in a peripheral edge of the first surface;
a wiring received in and connected to the peripheral recess of the first surface of the body;
a first layer having a first surface;
decoration formed on a periphery of the first surface of the first layer;
a second layer which is adhesive and has a first surface that adheres to the first surface of the body, a second surface that adheres to the first surface of the first layer, and a recess formed in a peripheral edge of the first surface of the second layer,
wherein the second layer has the same outer dimensions as the first layer; and
a third layer which is non-adhesive, is received in and adhered to the peripheral recess of the second layer, is formed between a portion of a periphery of the second layer and the decoration, is opposed to the wiring at the portion of the periphery of the second layer, and contacts the portion of the periphery of the second layer without adhering to the portion of the periphery of the second layer.

7. A touch panel, comprising:
a body having a first surface and containing a recess formed in a peripheral edge of the first surface;
a metal wiring received in and connected to the peripheral recess of the first surface of the body,
a first layer having a first surface;
a second layer which is adhesive, has a first surface that adheres to the first surface of the body, a second surface that adheres to the first surface of the first layer, and a recess formed in a peripheral edge of the first surface of the second layer;
decoration formed between the first surface of the first layer and the second surface of the second layer; and
a third layer which is non-adhesive, has a first surface and a second opposite surface, the first surface is received in and adhered to the peripheral recess of the second layer, and the second surface of the third layer contacts but is not adhered to the first surface of the second body or the wiring,
wherein the wiring extends out beyond the body and the first, second and third layers, and
wherein the non-adhesively connected second surface of the third layer isolates the wiring from movement of at least the second layer or the decoration caused by heat contraction of the second layer or the decoration layer, respectively.

8. A touch panel, comprising:
a body having a first surface and containing a first recess formed in a peripheral edge of the first surface;
a metal wiring received in the first recess and extending from the body;
a first layer having a first surface;
decoration formed on a periphery of the first surface of the first layer;
a second layer which is adhesive and has a first surface that adheres to the first surface of the body, and a second surface that adheres to the first surface of the first layer, and a recess formed in a peripheral edge of the first surface of the second layer; and
a third layer which is non-adhesive, is received in the second recess and contacts the metal wiring without adhering to the metal wiring.

\* \* \* \* \*